United States Patent [19]

Lorincz et al.

[11] 4,035,370

[45] July 12, 1977

[54] ALKALOID ESTERS

[75] Inventors: Csaba Lörincz; Egon Kárpáti; László Szporny; Kálmán Szász; Lajos Kisfaludy, all of Budapest, Hungary

[73] Assignee: Richter Gedeon Vegyeszeti Gyar Rt., Budapest, Hungary

[21] Appl. No.: 645,244

[22] Filed: Dec. 29, 1975

Related U.S. Application Data

[63] Continuation of Ser. No. 296,569, Oct. 11, 1972, abandoned.

[30] Foreign Application Priority Data

Nov. 3, 1971 Hungary .............................. RI 454

[51] Int. Cl.² ...................................... C07D 459/00
[52] U.S. Cl. ........................... 260/293.53; 424/267
[58] Field of Search ............................... 260/293.53

[56] References Cited

U.S. PATENT DOCUMENTS 3,454,583 7/1969 Kuehne ...................... 260/294.3

OTHER PUBLICATIONS

Trojanek et al., Tetra. Letters 20, 702–706 (1961).
Kisfaludy et al., Chem. Abstracts 73:35598k (1970).

Primary Examiner—Natalie Trousof
Attorney, Agent, or Firm—Karl F. Ross; Herbert Dubno

[57] ABSTRACT

Vasodilatory eburnamine-type alkaloid esters of the formula (I)

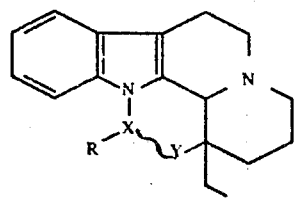

and salts and quaternary derivatives thereof, wherein $x \sim y$ represents a =CH=CH- or

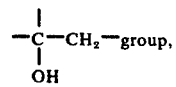

R represents a $C_{1-6}$ alkoxycarbonyl group optionally substituted with a hydroxy group or with a halogen atom, further an alkenyloxycarbonyl, aryloxycarbonyl, aralkoxycarbonyl group or an acylated primary alcohol group, especially apovincaninic acid ethyl ester, have been prepared by various methods of esterification.

1 Claim, No Drawings

ALKALOID ESTERS

This is a continuation, of application Ser. No. 296,569, filed Oct. 11, 1972, now abandoned. This invention relates to new eburnamine-type alkaloid esters and salts and pharmaceutical products containing the same, as well as to a process for the preparation thereof.

The novel compound according to the invention are represented by the formula (I)

wherein
$x \sim y$ represents a =C=CH- or $$-\underset{OH}{\overset{|}{C}}-CH_2-group,$$

and
R represents a $C_{1-8}$ alkoxycarbonyl group optionally substituted with a hydroxy group or with a halogen atom, further an alkenyloxycarbonyl, aryloxycarbonyl, aralkoxycarbonyl group or an acylated primary alcohol group.

There are some known derivatives of vincamine and some substances related to vincamine which possess pharmacological activites analogous to those of vincamine (e.g. Hungarian Patent Specifications No. 151,255, 157,687).

Now we have found that the novel eburnamine-type alkaloid esters of the formula (I) and their salts possess a substantially higher cerebral vasodilatory effect than vincamine.

Among the compounds prepared according to the invention, the following posses significant cerebral vasodilatory activity:
vincaminic acid ethyl ester,
vincaminic acid allyl ester,
vincaminic acid oxyethyl ester,
vincaminic acid chloroethyl ester,
vincaminic acid benzyl ester,
(+)-apovincaminic acid ethyl ester,
apovincaminic acid butyl ester,
acetic acid apovincaminol ester,
(−)-apovincaminic acid ethyl ester,
(+)-apovincaminic acid ethyl ester methoiodide.

Among the compounds listed above, (+)-apovincaminic acid ethyl ester, (−)-apovincaminic acid ethyl ester and (+)-apovincaminic acid ethyl ester methoiodide are the most preferred ones.

The results of the pharmacological tests carried out on the above compounds are listed in Tables 1 and 2, together with the corresponding data of vincamine. The investigations were carried out on narcotized dogs.

The arterial blood pressure was measured in the left arteria femoralis by an electromanometer. The cardial frequency was determined on the basis of the pulsatory component of the blood pressure. The number of respiration was measured with a pneumotachograph. The aortic flow (volume per minute) and the cerebral flow (arteria carotis internal and arteria vertebral flow on both sides) were measured with electromagnetic flowmeters situated on the respective parts of the body. The oxygen pressure of the arterial blood was measured in the arteria femoralis, while that of the cerebral venous blood in the sinus transversus. The circulation resistance of the total body and of the cerebral vascular system, the cerebral oxygen consumption and oxygen utilization, as well as the pressure output of the heart (cardial efficiency) were calculated on the basis of the above parameters which were measured continuously.

When comparing the effects of the compounds under examination with that of vincamine it turns out that the novel compounds have more advantageous effects than vincamine. The following advantages are to be mentioned:

1. The novel compounds have a more potent general vasodilatory effect than vincamine (determined on the basis of the vascular resistance of the total body).

2. They have a less marked blood pressure lowering effect than vincamine (determined on the basis of the medium arterial pressure).

3. Their cerebral vasodilatory activity exceeds that of vincamine (determined on the basis of the cerebral vascular resistance).

4. The cerebral vascular flow increases to a greater extent.

5. The pressure output of the heart (cardial efficiency) decreases.

6. The cardial frequency does not decrease but it increases.

7. The amount of blood forwarded by the heart per minute (volume per minute) does not decrease but it increases.

8. The cerebral oxygen consumption increases to a greater extent, accordingly the new compounds exert a more potent influence on the metabolism of the cerebral tissues than vincamine (see the data relating to the cerebral oxygen consumption).

On the basis of the above one can conclude that besides their potent vasodilatory activity, the novel compounds have also a desirable influence on the heart function, and stimulate the metabolism of the cerebral tissues by increasing the cerebral blood supply.

Table 1

| | The effect of vincamine and (−)-apovincaminic acid ethyl ester on the systemic circulation of dogs (Changes ± in %) | | | | | | | |
|---|---|---|---|---|---|---|---|---|
| | Vincamine | | | | (−)-apovincaminic acid ethyl ester | | | |
| Dose mg/kg | 0.5 | 1.0 | 2.0 | 4.0 | 0.5 | 1.0 | 2.0 | 4.0 |
| Medium arterial pressure | −4.76±1.38 | −12.26±1.66 | −19.88±2.09 | −34.04±1.94 | −1.45±0.86 | −10.70±1.85 | −16.73±2.33 | −14.22±0.54 |
| Cardiac frequency | −6.09±1.44 | −4.92±3.56 | −10.04±3.40 | −5.46±6.43 | 8.09±4.64 | 6.55±2.49 | 18.11±5.18 | 32.26±8.86 |
| Cardial | | | | | | | | |

Table 1-continued

The effect of vincamine and (−)-apovincaminic acid ethyl ester on the systemic circulation of dogs (Changes ± in %)

| Dose mg/kg | Vincamine | | | | (−)-apovincaminic acid ethyl ester | | | |
|---|---|---|---|---|---|---|---|---|
| | 0.5 | 1.0 | 2.0 | 4.0 | 0.5 | 1.0 | 2.0 | 4.0 |
| efficiency | −2.98±2.75 | −11.46±3.37 | −18.41±5.73 | −38.20±3.81 | — | −9.97±9.58 | −4.86±2.02 | — |
| Transported blood volume/minute | 0.34±0.34 | −6.95±2.27 | −5.45±4.86 | −12.26±4.77 | — | 10.97±5.49 | 12.93±6.95 | — |
| Vascular resistance of the total body | −4.70±2.28 | −9.47±4.31 | −10.08±4.39 | −14.34±5.44 | — | −18.33±5.83 | −24.53±8.70 | — |
| Cerebral arteriavenous oxygen difference | 3.34±4.06 | 5.95±3.81 | 17.55±9.47 | 29.13±7.35 | 3.10±12.64 | 9.68±3.95 | 13.05±10.4 | 22.31±25.80 |
| Cerebral oxygen consumption | 3.02±1.80 | 6.75±1.60 | 12.09±2.55 | 17.20±2.74 | 13.37±10.79 | 14.55±5.15 | 22.65±11.73 | 44.42±26.32 |
| Cerebral oxygen utilization | 0.40±2.82 | 11.56±6.70 | 28.70±11.32 | 29.68±8.29 | 3.09±12.60 | 9.69±3.96 | 13.06±3.27 | 22.31±25.79 |
| Cerebral vascular resistance | −3.28±1.39 | −8.85±2.06 | −15.69±2.75 | −13.76±3.37 | −6.38±4.12 | −11.50±1.82 | −17.82±3.27 | −19.25±4.04 |
| Cerebral vascular flow | 5.65±4.12 | 2.81±4.85 | 1.68±2.97 | 0.80±2.08 | 11.07±4.22 | 8.09±3.50 | 19.30±4.83 | 19.31±4.84 |
| Number of respiration | −0.65±0.42 | −1.56±1.17 | 6.84±2.25 | 2.18±1.43 | 0.66±1.23 | 8.71±2.51 | 6.92±3.14 | −9.49±5.21 |

Table 2

The effect of (+)-apovincaminic acid ethyl ester and of (+)-apovincaminic acid ethyl ester methoiodide on the systemic circulation of dogs (Changes ± in %)

| Dose mg/kg | (+)-apovincaminic acid ethyl ester | | | | | | (+)-apovincamin acid ethyl ester metho- | |
|---|---|---|---|---|---|---|---|---|
| | 0.1 | 0.2 | 0.5 | 1.0 | 2.0 | 4.0 | 1.0 | 2.0 |
| Medium arterial pressure | −4.77±1.16 | −9.87±1.65 | −17.57±2.56 | −26.71±2.45 | −35.84±1.83 | −44.61±2.06 | −13.41±3.11 | −17.54±4.12 |
| Cardiac frequency | 2.92−1.48 | 2.75±1.66 | 5.74±1.66 | 10.40±3.61 | 15.75±7.29 | 28.71±11.19 | 3.29±1.73 | 9.14±2.28 |
| Cardial efficiency | −12.17±9.16 | −10.51±7.67 | −9.64±2.05 | −17.72±3.51 | −14.31±2.94 | −23.91±6.15 | −5.89±1.73 | 11.27±3.44 |
| Transported blood volume/minute | −2.78±6.41 | −0.83±6.51 | 7.75±2.11 | 15.97±6.96 | 25.62±7.06 | 29.99±6.59 | 6.51±1.96 | 12.81±3.11 |
| Vascular resistance of the total body | −6.61±2.93 | 12.56±3.52 | −25.99±3.12 | −34.99±6.17 | −42.56±3.03 | −46.73±5.78 | −12.23±3.14 | 19.51±3.56 |
| Cerebral arteriavenous oxygen difference | 5.85±2.09 | 8.90±4.55 | 20.04±4.49 | 23.38±7.14 | 44.75±11.51 | 39.88±11.11 | 8.42±2.35 | 13.32±5.14 |
| Cerebral oxygen consumption | 6.38±2.65 | 11.57±3.54 | 8.13±2.74 | 10.91±3.46 | 13.22±2.11 | 12.17±3.91 | 5.43±1.85 | 7.37±2.51 |
| Cerebral oxygen utilization | 5.65±2.24 | 9.05±4.88 | 22.10±3.80 | 23.42±7.16 | 65.95±21.96 | 32.68±14.27 | 14.52±3.41 | 19.31±3.15 |
| Cerebral vascular resistance | −3.52±1.28 | 10.02±3.02 | −15.75±2.67 | −21.95±3.23 | −21.72±3.97 | −28.95±3.84 | −9.33±4.21 | −14.52±2.47 |
| Cerebral vascular flow | 2.05±1.98 | 8.25±3.66 | 16.54±6.02 | 15.07±4.44 | 16.18±2.04 | 23.16±4.37 | 5.15±2.33 | 7.24±2.14 |
| Number of respiration | 1.24±0.93 | 2.42±1.55 | 0.66±1.23 | 8.71±4.51 | 6.92±3.22 | −9.49±5.42 | 3.24±2.11 | 2.14±1.44 |

The novel alkaloid-ester derivatives of the formula (I), having pharmacological effects, can be prepared according to the invention by methods of esterification as listed below:

a. a salt of apovincaminic acid or vincaminic acid is reacted with a $C_{1-6}$ alkyl halide, a $C_{1-6}$ alkenyl halide, a $C_{1-6}$ alkyl halide substituted with one or more halogen or hydroxy groups, an aralkyl halide or aryl halide, or with the corresponding sulfates, or with diazomethane, or b. apovincaminic acid or vincaminic acid is esterified with a $C_{1-6}$ alcohol in the presence of one or more catalysts, preferably in the presence of ammonia, mineral or organic acids or aliphatic or aromatic sulfonic acids, or c. apovincamine or vincamine is reacted with an alkali metal alcoholate, or d. apovincaminic acid or vincaminic acid, or, respectively, apovincamine or vincamine is reacted with an ester of a $C_{1-6}$ carboxylic acid, or e. apovincaminic acid or vincaminic acid, or, respectively, apovincamine or vincamine is converted into the corresponding hydroxy derivative by reacting it with a reducing agent (preferably with one or more alkali metal hydrides), and the obtained compound is esterified with an anhydride or halide of a $C_{1-6}$ aliphatic carboxylic acid or of an aromatic carboxylic acid;

and, if desired, the thus-obtained eburnamine-type new alkaloid esters of the general formula (I) are converted into their acid addition salts or quaternary salts by reacting them with a mineral or organic acid (e.g. with hydrochloric, hydrobromic, sulfuric, phosphoric, acetic, citric, maleic, tartaric or malic acid) or with an alkyl halide, respectively, finally, if desired, the thus-obtained salts are converted into the free bases, and the free bases are converted into other salts thereof.

Variant (a) of the process of the invention is preferably carried out as follows: If the reagent is an alkyl-, alkenyl-, substituted alkyl-, aralkyl- or aryl halide, anhydrous alcohol or an excess of the appropriate halide is used as reaction medium. If esterification is carried out with diazomethane or with an alkyl sulfate, the reaction may be conducted in an anhydrous alcohol or ether, in acetone, or in anhydrous tetrahydrofuran as well. In each of the cases, esterification is carried out by boiling the reaction mixture under reflux for several hours. The separation of the crystalline ester is carried out by phase exchange purification, as follows: the reaction mixture is concentrated under reduced pressure, the concentrate is diluted with an aqueous solution of an acid, the aqueous-acidic mixture is rendered alkaline, the product is extracted into an organic solvent, the organic solution is concentrated, and the residue is recrystallized. In this procedure, crystalline compounds of the general formula (I) are obtained.

Variant (b) of the process of the invention is preferably carried out in the presence of a solvent. As solvents, e.g. an excess of the appropriate alcohol, and/or anhydrous benzene or toluene may be used. The alkaline catalyst may be ammonia, while the acidic catalyst may be ethanesulfonic acid. The reaction is carried out by boiling the mixture under reflux for several hours. The obtained ester is separated and purified by phase exchange.

Variant (c) of the process of the invention is carried out preferably in an apolar solvent or solvent mixture (most preferred in benzene). The reaction mixture containing an alkali metal alcoholate — preferably sodium alcoholate — is boiled under reflux for several hours, thereafter the obtained product is separated and purified by phase exchange.

Variant (d) of the process of the invention is preferably carried out in the presence of a solvent or solvent mixture, particularly in the presence of an alcohol and/or in the presence of excessive amounts of the appropriate ester reagent. The reaction is carried out as described at variant (c).

Variant (e) of the process of the invention is carried out as follows: vincamine or apovincamine, or vincaminic acid or apovincaminic acid, respectively, or the alkali metal salt of these compounds is reacted with a reducing agent, preferably with an alkali metal hydride in the presence of an anhydrous organic solvent, preferably in ether or tetrahydrofuran. The obtained hydroxy derivative is dissolved in pyridine and/or in a chlorinated hydrocarbon, the solution is cooled, and an acid halide or acid anhydride is added to the solution. Esterification is carried out at a temperature below room temperature. The obtained ester derivative is separated and purified by the phase exchange method mentioned above.

The novel compounds of the invention can be used in the therapy in the form of pharmaceutical preprations. These pharmaceutical preparations may contain indifferent organic or mineral carriers suitable for enteral or parenteral administration, which do not enter into reaction with the new ester derivatives.

The pharmaceutical products may contain the new compounds alone or together with other known active agents, e.g. in combination with reserpine.

The pharmaceutical products may be sterilized if desired. The compositions may also contain other auxiliary substances, e.g. salts for adjusting the osmotic pressure to the desired value, buffers, etc.

The invention is further elucidated by the aid of the following non-limiting Examples.

EXAMPLE 1

Vincaminic acid ethyl ester 1 g. (0.0029 moles) of vincaminic acid and 0.11 g. (0.0027 moles) of sodium hydroxide are dissolved in 50 ml. of anhydrous ethanol. 0.35 g. (0.0029 moles) of ethyl bromide are added to the solution, and the reaction mixture is boiled under reflux for 2 hours. During this period, crystalline substance starts to separate from the solution. The formed crystals are dissolved by adding 0.1 g. of sodium hydroxide. Thereafter a further amount of 0.10 g. of ethyl bromide are added to the solution, and the reaction mixture is boiled under reflux for additional 2 hours. The solution is cooled and evaporated to dryness under reduced pressure. The dry residue is dissolved in 300 ml. of methylene chloride, and this solution is extracted with 100 ml. of 5% aqueous sodium hydroxide solution in order to remove the non-reacted vincaminic acid and the sodium chloride formed in the reaction. The organic phase is separated and dried over anhydrous potassium carbonate. The mixture is filtered and the filtrate is evaporated to dryness under reduced pressure. The dry residue is dissolved in 20 ml. of methanol and the solution is left to stand at 0° to 2° C for about 10 hours. The separated crystalline product is purified by recrystallization from anhydrous ethanol.

0.82 g. (82%) of vincaminic acid ethyl ester are obtained. The product is uniform on the basis of layer chromatography. M.p.: 244° C (Boetius). $[\alpha]_d^{20} = +63.6°$ ($c = 1$, in pyridine).

Elementary analysis: Calculated: C = 71.71% H = 7.66% N = 7.60%; Found: C = 72.03% H = 8.28% N = 7.47%.

The structure of the product is identified by its IR spectrum (an ester band appears at 5.71 $\mu$).

EXAMPLE 2

Vincaminic acid allyl ester 1 g. (0.0029 moles) of vincaminic acid and 0.11 g. (0.0027 moles) of sodium hydroxide are dissolved in 120 ml. of anhydrous ethanol. 0.5 g. (0.0041 moles) of allyl bromide are added to the solution, and the reaction mixture is boiled under reflux for 1 hour. The formation of vincaminic acid allyl ester is monitored by layer chromatography. When the spot of vincaminic acid disappears, the boiling is terminated. The solution is cooled and evaporated to dryness. The dry residue is dissolved in 200 ml. of 2% aqueous sulfuric acid, and the solution is extracted with 2×200 ml. of benzene. The pH of the separated aqueous phase is adjusted to 8 with 5% aqueous ammonia, thereafter the slightly alkaline solution is extracted with 5×200 ml. of benzene. The obtained organic solution is dried over anhydrous potassium carbonate, filtered and evaporated to dryness. The dry residue is dissolved in 10 ml. of anhydrous ethanol, and this solution is left to stand at 0° to 2° C for about 10 hours. The separated crystals are filtered off and recrystallized from anhydrous ethanol. 0.84 g. of vincaminic acid allyl ester are obtained (yield: 84%). On the basis of layer chromatography, an uniform product is obtained. M.p.: 236° C (Boetius).

Elementary analysis: Calculated: C = 72.60% H = 7.41% N = 7.39%; Found: C = 72.48% H = 7.40% N = 7.41%.

The structure of the product is identified by its IR spectrum (an ester band appears at 5.72 $\mu$).

EXAMPLE 3

Vincaminic acid oxyethyl ester 1 g. (0.0029 moles) of vincaminic acid and 0.11 g. (0.0027 moles) of sodium hydroxide are suspended in 10 ml. of ethylene chlorohydrine, thereafter the solids are dissolved in the reaction medium by heating. The solution is boiled under reflux for 3 hours. The formation of the ester is monitored by layer chromatography. When the spot characteristic to vincaminic acid disappears, the boiling is ceased. The solution is cooled, and 500 ml. of a 2% aqueous sulfuric acid is added to it. The pH of the acidic solution is adjusted to 8 by adding an 5% aqueous sodium hydroxide solution. A precipitate separates. The mixture is extracted with 5×200 ml. of benzene. The organic solution is separated, dried over anhydrous potassium carbonate and filtered. The benzene solution is evaporated to dryness, and the residue is crystallized from 10 ml. of ether. The etheral solution is left to stand for 10 hours, thereafter the separated crystals are filtered off and recrystallized from anhydrous methanol.

0.72 g. (72%) of vincaminic acid oxyethyl ester are obtained. On the basis of layer chromatography, a uniform product is formed. M.p.: 171° C (Boetius).

Elementary analysis: Calculated: C = 68.66% H = 7.36% N = 7.32% Found: C = 69.28% H = 7.86% N = 7.58%

The structure of the product is identified by its IR-spectrum (an ester band appears at 5.79 $\mu$).

EXAMPLE 4

Vincaminic acid chloroethyl ester 1 g. (0.0029 moles) of vincaminic acid and 0.11 g. (0.0027 moles) of sodium hydroxide are dissolved in 80 ml. of anhydrous ethanol. The solution is evaporated to dryness under reduced pressure. The dry residue is dissolved in 40 ml. of anhydrous acetonitrile, and 20 ml. of 1,2-dichloroethane are added to the solution. The obtained mixture is refluxed for 4 hours. The formation of the ester is monitored by layer chromatography. When the spot characteristic to vincaminic acid dissappears, the boiling is ceased. The solution is evaporated to dryness under reduced pressure, and the dry residue is dissolved in 200 ml. of 2% aqueous sulfuric acid. The pH of the acidic solution is adjusted to 8 with 5% aqueous sodium hydroxide solution. A precipitate separates. The mixture is extracted with 5×200 ml. of benzene, and the organic phase is dried over anhydrous potassium carbonate. The benzene solution is filtered, and the filtrate is evaporated to dryness under reduced pressure. The dry residue is crystallized from 10 ml. of ether, and the obtained crystals are recrystallized from anhydrous methanol.

0.68 g. (68%) of vincaminic acid chloroethyl ester are obtained. On the basis of layer chromatography, a uniform product is formed. M.p.: 218° C (Boetius).

Elementary analysis: Calculated: C = 65.58% H = 6.75% N = 6.95% Found: C = 65.21% H = 6.52% N = 6.89%

The structure of the compound is identified on the basis of its IR-spectrum (an ester band appears at 5.72 $\mu$).

EXAMPLE 5

Vincaminic acid benzyl ester tartrate 1 g. (0.0028 moles) of vincamine is dissolved in 125 ml. of anhydrous benzene, and 3 ml. of sodium benzylate solution are added to the above solution. (The solution of sodium benzylate is prepared from 10 ml. of benzyl alcohol and 0.2 g. of metallic sodium in a known way.) The solution is boiled under reflux for 2 hours. The reaction is monitored by layer chromatography. If the chromatographical analysis shows an incomplete reaction, further 1 ml. of sodium benzalate solution is added to the mixture, and the mixture is boiled for a further hour. When the reaction is complete, 300 ml. of benzene are added to the solution, and the mixture is extracted with 200 ml. portions of 2% aqueous sulfuric acid until the acidic phase does not show a positive Mayer reaction. The aqueous phase is separated. The pH of the aqueous phase is adjusted to 8 with 5% aqueous sodium hydroxide solution, and the alkaline solution is extracted with 5×20 ml. of dichloromethane. The organic solutions are combined and dried over anhydrous potassium carbonate. The solution is filtered and evaporated to dryness. The dry residue is dissolved in 15 ml. of ether, and a saturated etheral solution of tartaric acid is added to it in an amount sufficient to adjust the pH of the mixture to 3. The solution is left to crystallize for about 10 hours. The white, crystalline vincaminic acid benzyl ester tartrate is filtered off and recrystallized from acetone. 0.74 g. (74%) of vincaminic acid benzyl ester tartrate are obtained. On the basis of layer chromatography, a uniform product is formed. M.p.: 115° C (Boetius).

Elementary analysis: Calculated: C = 64.12% H = 6.25% N = 4.82%; Found: C = 63.98% H = 6.33% N = 5.02%.

The structure of the product is identified on the basis of its IR spectrum (an ester band appears at 5.75 $\mu$).

EXAMPLE 6

Apovincaminic acid ethyl ester a. 1 g. (0.0031 moles) of apovincaminic acid and 0.17 g. (0.003 moles) of potassium hydroxide are dissolved in 80 ml. of anhydrous ethanol, thereafter 0.4 g. (0.0036 moles) of ethyl bromide are added to the solution. The solution is boiled under reflux for 3 hours. The reaction is monitored by layer chromatography. The solution is cooled and evaporated to dryness under reduced pressure. The dry residue is dissolved in 500 ml. of 2% aqueous sulfuric acid, and the solution is filtered. The pH of the filtrate is adjusted to 8 with 5% aqueous sodium hyrodxide solution. A small amount of precipitate separates. The mixture is extracted with 200 ml. portions of methylene chloride until no positive Mayer reaction can be observed in the aqueous phase. The organic phases are separated, combined, dried over anhydrous potassium carbonate, filtered and evaporated to dryness under reduced pressure. The dry residue is dissolved in 10 ml. of anhydrous ethanol, and the solution is left to crystallize at 0° to 2° C for 10 hours. 0.66 g. of apovincaminic acid ethyl ester are obtained (yield: 66%). On the basis of layer chromatography, a uniform product is formed. M.p.: 144° C (Boetius).

Elementary analysis: Calculated: C = 75.40% H = 7.48% N = 7.99%; Found: C = 75.20% H =7.52% N = 8.02%.

The structure of the product is identified on the basis of its IR spectrum (an ester band appears at 5.75 $\mu$).

b. 1 g. (0.0029 moles) of vincaminic acid and 0.11 g. (0.0027 moles) of sodium hydroxide are dissolved in 200 ml. of abs. ethanol. The solution is heated to reflux, and when boiling sets in, 10 ml. of concentrated ethanesulfonic acid are added to the solution. The formation of apovincaminic acid ethyl ester is monitored by layer chromatography. After 3 hours of boiling, the solution is concentrated to about 20 ml. under reduced pressure. 500 ml. of distilled water are added to the concentrate, and the mixture is placed into a separatory funnel. The pH of the solution is adjusted to 8 with 5% aqueous sodium hydroxide solution. A precipitate separates. The mixture is extracted with 5×200 ml. of methylene chloride, and the organic solution is dried over anhydrous potassium carbonate. The solution is filtered and evaporated to dryness under reduced pressure. The dry residue is dissolved in 20 ml. of ethanol, and the solution is left to crystallize at 0 to 2° C. 0.86 g. (86%) of apovincaminic acid ethyl ester are obtained. On the basis of layer chromatography, a uniform product is formed. M.p.: 144° C (Boetius).

EXAMPLE 7

Apovincaminic acid butyl ester 1 g. (0.0031 moles) of apovincaminic acid and 0.12 g. (0.003 moles) of sodium hydroxide are dissolved in 80 ml. of anhydrous ethanol, thereafter 0.5 g. (0.003 moles) of butyl bromide are added to the solution. The solution is boiled under reflux for 4 hours. The reaction is monitored by layer chromatography. When the reaction is complete, the solution is cooled and evaporated to dryness under reduced pressure. The dry residue is dissolved in 500 ml. of 2% aqueous sulfuric acid, and the pH of the aqueous solution is adjusted to 8 by adding 5% aqueous sodium hydroxide solution. The obtained alkaline solution is extracted with 5×200 ml. of benzene. The benzene solutions are combined, dried over anhydrous potassium carbonate, filtered and evaporated to dryness under reduced pressure. The dry residue is crystallized from 10 ml. of ether. The obtained crystalline substance is recrystallized from acetone.

0.70 g. (70%) of apovincaminic acid butyl ester are obtained. On the basis of layer chromatography, a uniform product is formed. M.p.: 175° C (decomposition) (Boetius).

Elementary analysis: Calculated: C = 76.15% H = 7.99% N = 7.40% Found: C = 76.18% H = 7.83% N = 7.39%

The structure of the product is identified on the basis of its IR spectrum (an ester band appears at 5.75 $\mu$).

EXAMPLE 8

Acetic acid ester of apovincaminol

Apovincamine is reduced to apovincaminol according to known methods, using lithium aluminum hydride. 1 g. (0.0032 moles) of apovincaminol are dissolved in 50 ml. of anhydrous chloroform, and the solution is cooled to 0° C. 0.5 ml. of acetyl chloride are added to the cold solution, and the reaction mixture is left to stand at 0° C for 2 hours. The formation of the ester compound is monitored by layer chromatography.

500 ml. of chloroform are added to the solution containing the ester derivative, and the mixture is shaken for a long period with 300 ml. of 5% aqueous sodium hydroxide solution. The chloroform phase is separated and dried over anhydrous potassium carbonate. The filtered organic solution is evaporated to dryness under reduced pressure. The dry residue is dissolved in 500 ml. of benzene, and the solution is subjected to chromatography on a column containing 300 g. of alumina (III activity grade). The eluate is collected into 100 ml. fractions. Fractions Nos. 6 to 14 are combined and evaporated to dryness under reduced pressure. The dry residue is dissolved in 15 ml. of ether and a saturated etheral solution of tartaric acid is added to it in an amount sufficient to adjust the pH of the mixture to 3. The solution is left to crystallize at 0° to 2° C for 10 hours. The obtained ester derivative is filtered off.

0.67 g. (67%) of apovincaminol acetic acid ester are obtained. On the basis of layer chromatography, a uniform product is formed. M.p.: 209° C (Boetius).

Elementary analysis: Calculated: C = 62.38% H = 6.44% N = 5.60%; Found: C = 62.28% H = 6.41% N = 5.62%.

The structure of the compound is identified by its IR spectrum (an ester band appears at 5.67 $\mu$).

EXAMPLE 9

(-)-Apovincaminic acid ethyl ester 1 g. (0.0028 moles) of (-)-vincamine [$\alpha$] = 40.0°, m.p.: 231° C (Boetius)) is dissolved in 25 ml. of methanol containing 0.41 g. (0.007 moles) of potassium hydroxide under heating. The solution is boiled under reflux for 5 hours. during this time the saponification of the methyl ester is monitored by layer chromatography. If the reaction is incomplete at the end of the above period, the boiling of the mixture is continued. When the saponification is complete, the solution is cooled and adjusted to a neutral pH with glacial acetic acid. (-)-Vincaminic acid starts immediately to crystallize. The solution is left to crystallize for 12 to 14 hours at 0° to 2° C, thereafter the crystalline substance is filtered off. 0.95 g. (98%) of (-)-vincaminic acid are obtained. [$\alpha$] = −85.2° ($c$ = 1, in 0.1 n sodium hydroxide solution), m.p.: 257° C (Boetius).

The obtained (-)-vincaminic acid is dissolved in a mixture of 40 ml. of anhydrous ethanol and 3 ml. of concentrated (97%) sulfuric acid. The solution is refluxed for 8 hours. During this period the reaction is monitored by layer chromatography. When the reaction is complete, the solution is cooled, evaporated to 7 ml. under reduced pressure, and the residue is transferred into a separatory funnell with 100 ml. of distilled water. The pH of the solution is adjusted to 8.5 with 10% aqueous sodium hydroxide solution. A precipitate separates. The mixture is extracted with 5×30 ml. of dichloromethane. The organic phases are combined, dried over anhydrous potassium carbonate, the drying agent is filtered off, and the filtrate is evaporated to dryness under reduced pressure. The oily residue is dissolved in 15 ml. of anhydrous ethanol. (-)-Apovincaminic acid ethyl ester starts to crystallize immediately. The mixture is left to crystallize for 8 to 10 hours at 0° to 2° C, and the crystalline substance is filtered off. 0.71 g. (75%) of (-)-apovincamic acid ethyl ester are obtained. M.p.: 153° C (Boetius). [α] = −112.5° (c = 1, in pyridine).

EXAMPLE 10

Apovincaminic acid ethyl ester methoiodide 1 g. (0.0028 moles) of apovincaminic acid ethyl ester is dissolved in 25 ml. of anhydrous acetone, and 0.44 g. (0.003 moles) of methyl iodide are added to the solution. The mixture is left to stand at room temperature for 24 hours. During this period the reaction is monitored by layer chromatography. Needle crystals start to separate from the reaction mixture even when standing at room temperature. The mixture is evaporated under reduced pressure to a final volume of about 10 ml., and the concentrate is left to crystallize at 0° to 2° C for about 8 to 10 hours. The crystals are filtered off and washed with a few amount of cold acetone. 1.29 g. (92%) of apovincaminic acid ethyl ester methoiodide are obtained. M.p.: 204° C.

Elementary analysis: Calculated: C = 56.12% H = 5.93% N = 5.69% I = 25.77% Found: C = 56.02% H = 5.88% N = 5.70% I = 25.79%

EXAMPLE 11

| Tablets containing apovincaminic acid ethyl ester Composition: | |
|---|---|
| apovincaminic acid ethyl ester | 0.005 g. |
| gelatine | 0.002 g. |
| magnesium stearate | 0.002 g. |
| talc | 0.003 g. |
| starch | 0.040 g. |
| lactose | 0.093 g. |

The tablets of the above composition are prepared as follows: The active agent, starch and lactose are homogenized, and the homogeneous mixture is kneaded with an aqueous solution of gelatine. The mass is granulated, the wet granules are dried at 30° to 50° C, thereafter talc and magnesium stearate are added to the dry granules. The mass is homogenized, and the homogeneous mass is compressed into tablets.

What we claim is:

1. Apovincaminic acid ethyl ester.

* * * * *